(12) United States Patent
Fadler et al.

(10) Patent No.: US 7,810,995 B2
(45) Date of Patent: Oct. 12, 2010

(54) DISPLACEMENT FOR AN X-RAY C-ARM

(75) Inventors: Franz Fadler, Hetzles (DE); Norbert Herrmann, Ebnath (DE); Manfred Sechser, Neusorg (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 12/472,957

(22) Filed: May 27, 2009

(65) Prior Publication Data

US 2009/0296892 A1 Dec. 3, 2009

(30) Foreign Application Priority Data

Jun. 3, 2008 (DE) ........................ 10 2008 026 622

(51) Int. Cl.
*H05G 1/02* (2006.01)
(52) U.S. Cl. ...................................... 378/197
(58) Field of Classification Search ......... 378/193–198, 378/167, 189, 204
See application file for complete search history.

(56) References Cited

U.S. PATENT DOCUMENTS 6,609,826 B1    8/2003  Fujii et al. ................... 378/198

FOREIGN PATENT DOCUMENTS

| DE | 34 07 338 C1 | 6/1985 |
| DE | 10 2005 012 700 A1 | 9/2006 |
| DE | 10 2008 015 341 A1 | 9/2008 |

*Primary Examiner*—Courtney Thomas
(74) *Attorney, Agent, or Firm*—Brinks Hofer Gilson & Lione

(57) ABSTRACT

The present embodiments relate to a displacement apparatus for a C-arm arranged on a trolley. The displacement apparatus includes at least a first and at least a second guide element arranged in a plane, whereby the first and second guide elements are arranged at right angles to one another, a first displacement device which can be moved along the first guide element, and a second displacement device, which can be moved along the second guide element. A linking device connects the first and second displacement device in such a way that any movement of the first displacement device will result in the second displacement device being moved along the second guide element. This avoids the possibility of any jamming which may arise as a consequence of the leverage forces generated when a C-arm is moved.

11 Claims, 5 Drawing Sheets

DISPLACEMENT FOR AN X-RAY C-ARM

The present patent document claims the benefit of German Patent Application DE 10 2008 026 622.1 filed on Jun. 3, 2008, which is hereby incorporated by reference.

BACKGROUND

Mobile x-ray devices with C-arms are used frequently in surgical interventions in operating rooms. The extensive mobility of the C-arm x-ray systems allows staff to move the C-arm x-ray system away from and back to the patient on the operating table while an operation is in progress. It is beneficial, especially during use in small operating rooms, not to have to move the relatively heavy C-arm x-ray systems in the entirety too often. It is preferable to move the C-arm, having an x-ray emitter and x-ray detector, only within certain confines, rather than the entire C-arm system. Positions which have already been assumed by the C-arm system can be reassumed automatically and precisely.

U.S. Pat. No. 6,609,826 B1 describes the way in which a C-arm can be moved horizontally to and in parallel with a patient support. U.S. Pat. No. 6,609,826 B1 discloses a moving apparatus between a C-arm and a retaining device. The C-arm is moveable in a horizontal direction at right angles to one arm. However, the parallel linear guides used and the weight of the C-arm can cause the moving apparatus to jam as a consequence of the unfavorable leverage ratio between the displacement force applied and the distance to the linear guides.

SUMMARY AND DESCRIPTION

The present embodiments may obviate one or more of the limitations or drawbacks inherent in the related art. For example, in one embodiment, a displacement apparatus allows an x-ray C-arm to be moved in parallel with the patient support.

In one embodiment, a displacement apparatus for a C-arm arranged on a trolley (carriage) is provided. The displacement apparatus includes at least a first and at least a second guide element arranged in a single plane or in parallel with a single plane. The first and the second guide elements may be arranged at rights angles to one another, along with a first displacement device which can be moved along the first guide element and a second displacement device which can be moved along the second guide element. A linking device connects the first and second displacement device to one another such that the second displacement device is moved along the second guide element when the first displacement device is moved. This avoids the possibility of any jamming which may arise as a consequence of the leverage forces exerted when a C-arm is moved, such as can occur with parallel linear guides.

The plane may be aligned horizontally. This facilitates displacement in parallel with the ground and/or with a patient support.

In another embodiment, part of the leverage force applied to the first displacement device can be applied to the second displacement device. Accordingly, the transmission of force is optimized and does not jam.

Furthermore, the force applied to the second displacement device can be transferred to the second guide element. This ensures optimum dissipation of power.

The first displacement device may include a first slide which can travel within or on the first guide element. The second displacement device may include a second slide which can travel within or on the second guide element. This is a cost-effective implementation.

The linking device may be a parallel rocker, whereby the levers on the parallel rocker are articulated on the first and second displacement device. This makes for straightforward and cost-effective construction of the displacement apparatus.

In one embodiment, the first guide element may include a first rail system and the second guide element may include a second rail system. This is also a cost-effective implementation of the displacement apparatus.

The first displacement device may be moved approximately +/200 mm around a central location. This enables a C-arm to be moved sufficiently along a patient support.

Furthermore, the first displacement device can be moved by a belt drive that is actively connected to the first displacement device. This provides a straightforward and cost-effective drive system.

In one embodiment, a C-arm includes a displacement apparatus. The C-arm is arranged on the first displacement device in such a way that it can be moved in parallel with a patient support. The C-arm may be used automatically and easily in a repositionable fashion in the operating room.

In another embodiment, an x-ray apparatus includes a C-arm having the displacement apparatus.

DETAILED DESCRIPTION

Figure 1:
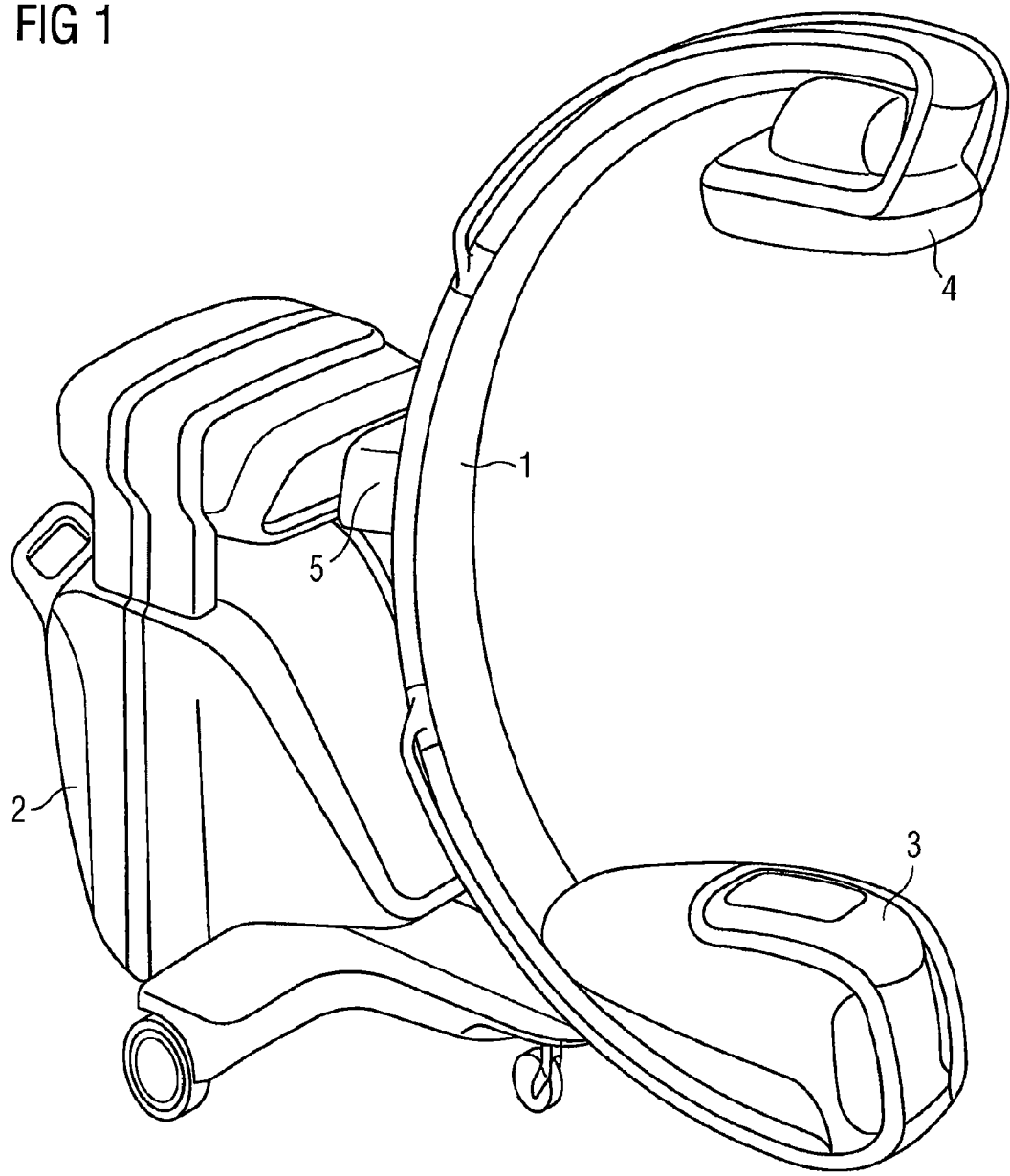
FIG. 1 shows one embodiment of a mobile C-arm x-ray device.

FIG. 1 shows a mobile C-arm x-ray system. An x-ray C-arm 1 is arranged on a trolley 2 with rollers. The x-ray C-arm 1 and the trolley 2 are connected to one another by a C-arm retaining module 5. An x-ray emitter 3 and an x-ray detector 4 are located at the ends of x-ray C-arm 1. For example, a patient on a support can be x-rayed with the x-ray emitter 3. The x-rays from the x-ray emitter 3 may be absorbed by the x-ray detector 4. The x-ray C-arm 1, which is connected to the C-arm retaining module 5, can be moved horizontally using a displacement apparatus.

Figure 2:
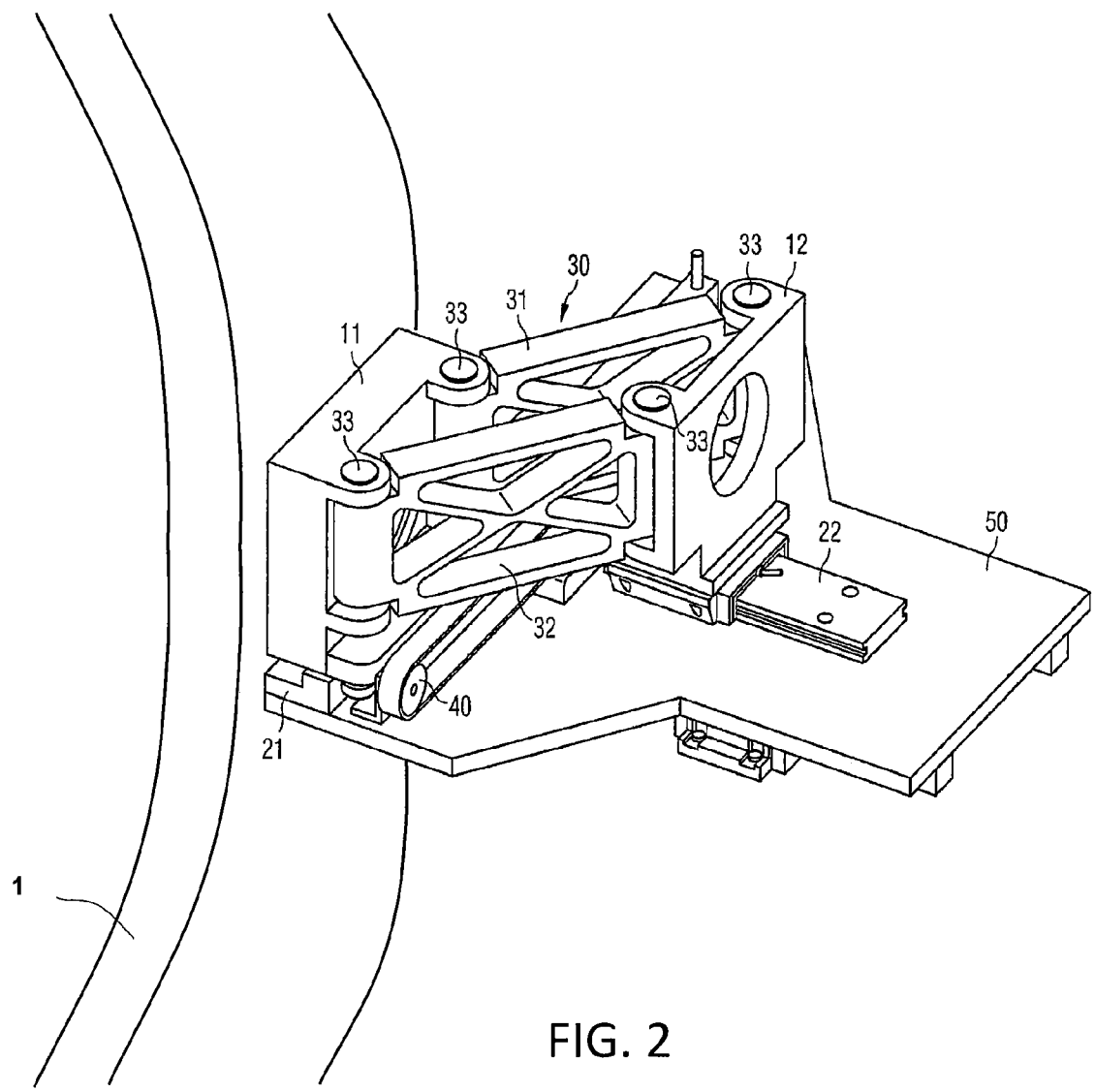
FIG. 2 shows a perspective view of one embodiment of a displacement apparatus with a parallel rocker.
Figure 3:
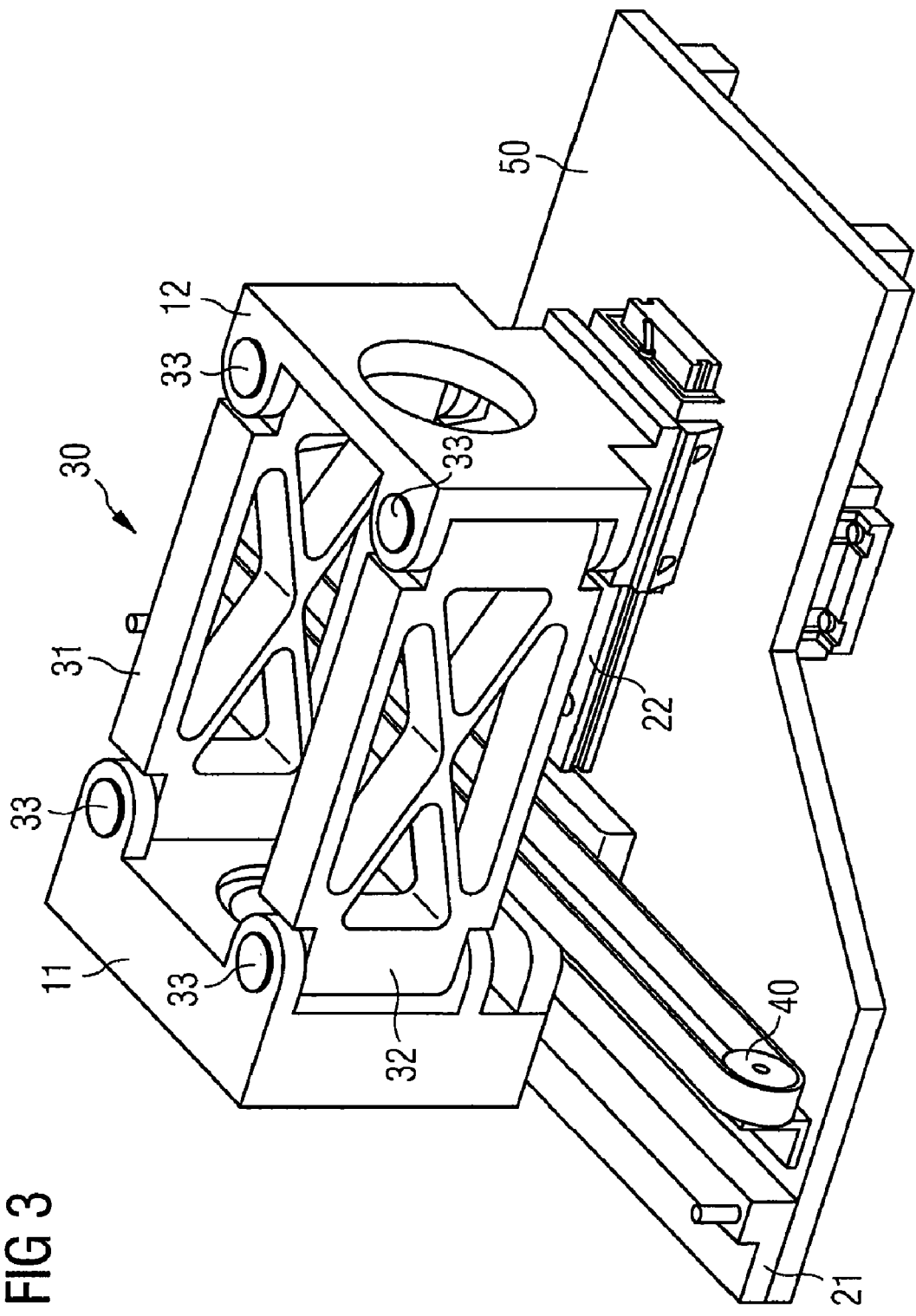
FIG. 3 shows another perspective view of the displacement apparatus with a parallel rocker.
Figure 4:
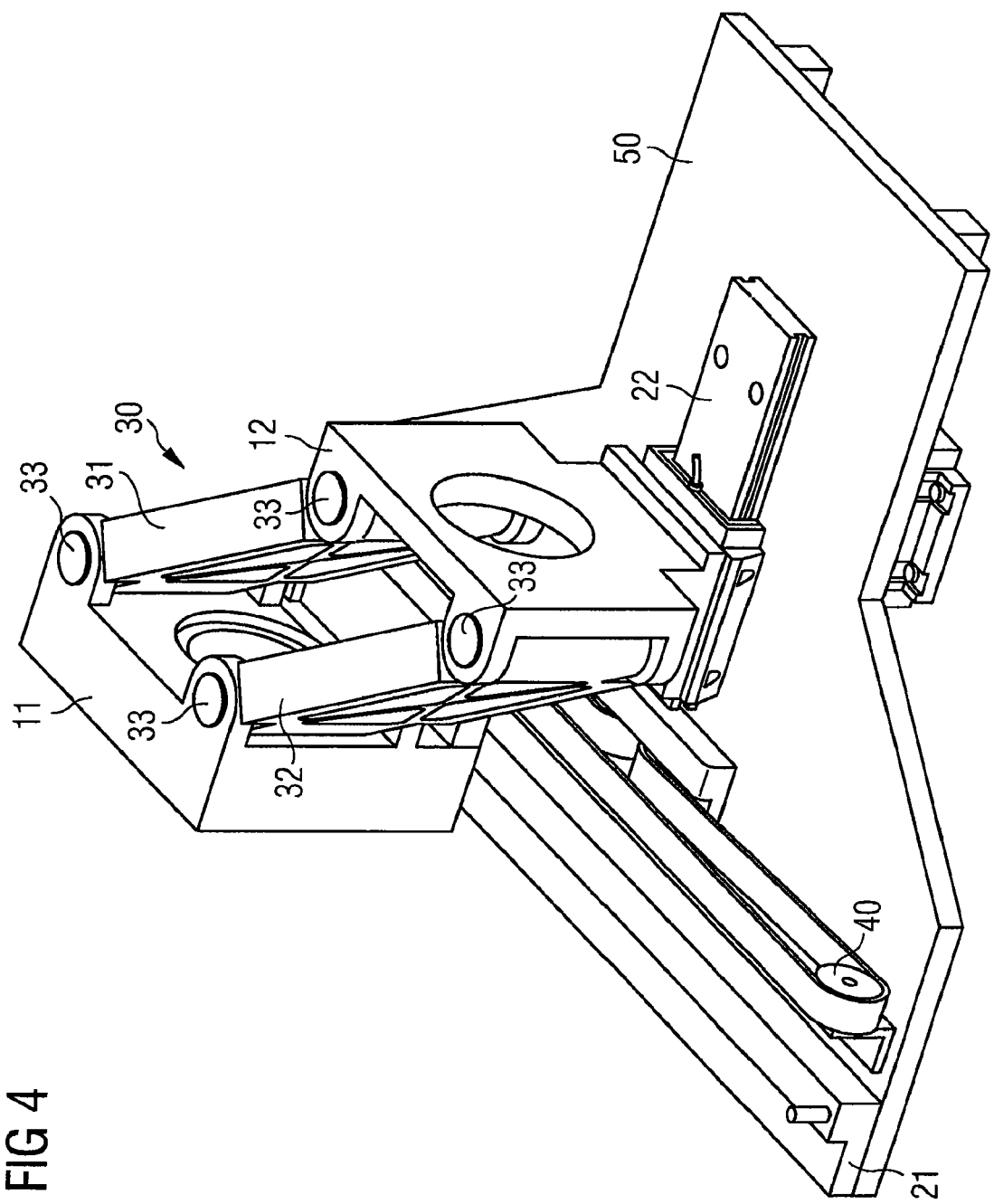
FIG. 4 shows another perspective view of the displacement apparatus with a parallel rocker.

FIGS. 2, 3 and 4 show a displacement apparatus in various positions. The displacement apparatus includes a carrier plate 50, upon which are arranged a first guide element 21 and, vertical to it in the same plane, or in parallel with this plane, a second guide element 22. The two guide elements 21, 22 may, for example, take the form of a rail system or a grooved plate. A first displacement device 11, such as a first carriage, may be arranged in a displaceable fashion on the first guide element 21. A second displacement device 12, such as a second carriage, may be arranged in a displaceable fashion on the second guide element 22.

A parallel rocker 30 may include a first and a second lever, 31, 32. The parallel rocker 30 may link the two displacement devices 11, 12 to one another. The connection between the first displacement device 11 and the second displacement device 12 may allow movement of the first displacement device 11 along the first guide element 21 to be converted into a movement of the second displacement device 12 along the second guide element 22. The two levers 31, 32 in the parallel rocker 30 are arranged on the displacement device 11, 12 by pivot bearings 33.

A belt drive 40 allows the first displacement device 11 to be moved along the first guide element 21. An x-ray C-arm can be attached to the front of the first displacement device 11 with a coupling element 13. The displacement apparatus may be used to move the x-ray C-arm in parallel with a patient support and/or with a patient.

FIG. 2 shows the displacement device 11 in an elevated position. FIG. 3 shows the displacement device 12 in an end position on the second guide element 22. The displacement device 11 may be in a central location, as shown in FIG. 2. FIG. 4 shows the displacement apparatus in a more elevated position. The first displacement device 11 is in an elevated position in symmetry with the central location. The second displacement device 12 has reached a second end position on the second rail system 22.

Figure 5:
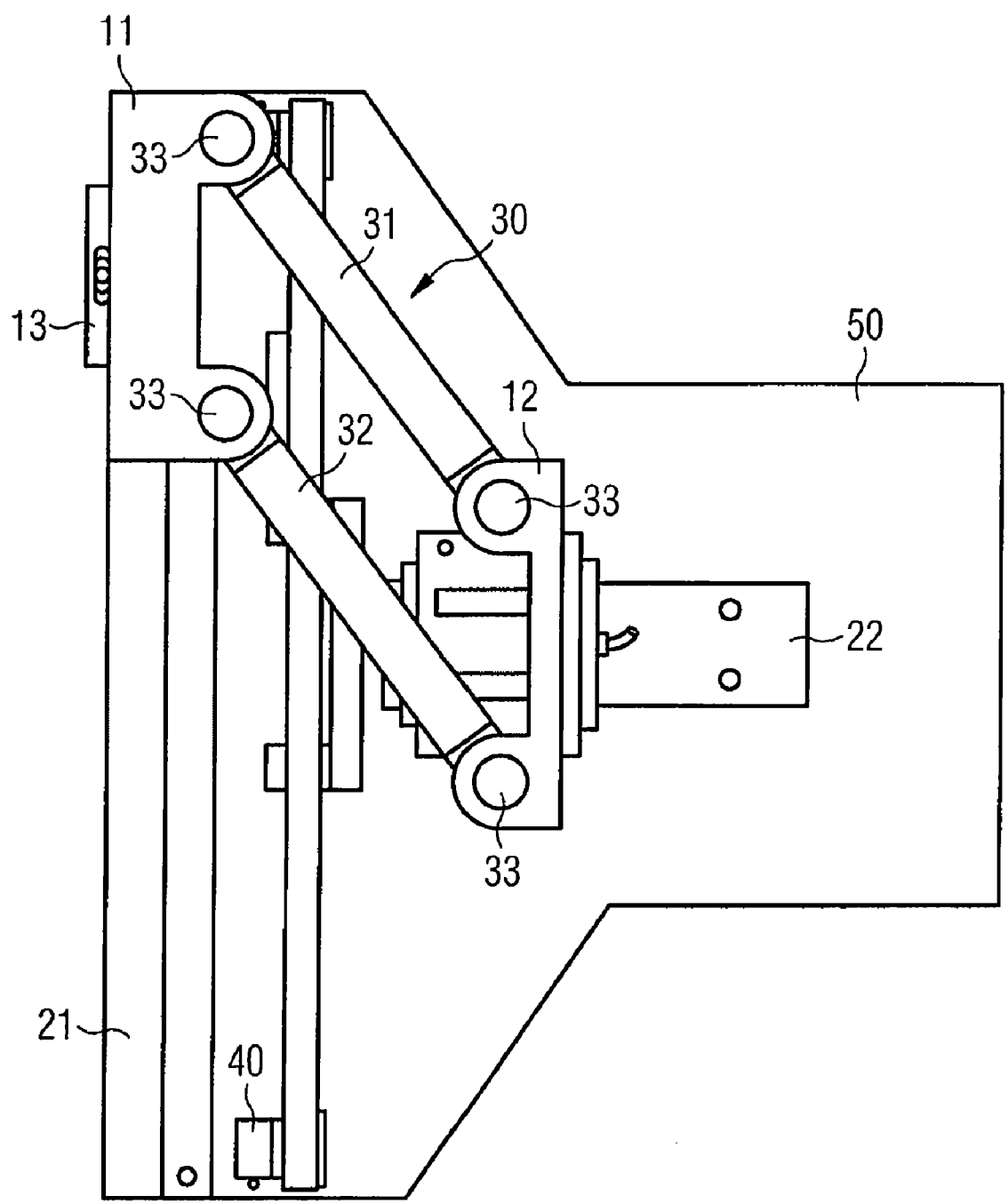
FIG. 5 shows a top view of the displacement apparatus with a parallel rocker.

FIG. 5 shows a top view of the displacement apparatus in an elevated position. A first guide element 21 and a second guide element 22 arranged at right angles thereto are arranged on a retaining plate 50. A first displacement device 11 is arranged on the first guide element 21. This is connected to a second displacement device 12 by a parallel rocker 30, made up of a first lever 31 and a second lever 32 and the pivot bearing 33. The second displacement device 12 is fixed to the second guide element 22 in a displaceable fashion. An x-ray C-arm may be mounted on a coupling element 13 connected with the first displacement device 11. The leverage forces generated by the weight of the x-ray C-arm are transferred from the first displacement device 11 to the second displacement element 12 by the parallel rocker 30. The force is then dissipated into the second guide element 22. The vertical alignment of the guide elements 21, 22 prevents the leverage forces from causing any jamming.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. A displacement apparatus for a C-arm arranged on a trolley, the displacement apparatus comprising:
   a first guide element and a second guide element arranged in a single plane or in parallel to a single plane, the first and second guide elements being in vertical alignment with one another,
   a first displacement device arranged in a displaceable fashion along the first guide element,
   a second displacement device arranged in a displaceable fashion along the second guide element, and
   a linking device that connects the first and second displacement devices to one another in such a way that any movement in the first displacement device causes the second displacement device to move along the second guide element.

2. The displacement apparatus as claimed in claim 1, wherein the plane is aligned horizontally.

3. The displacement apparatus as claimed in claim 1, wherein a leverage force acting on the first displacement device can be introduced to the second displacement device.

4. The displacement apparatus as claimed in claim 3, wherein the leverage force applied to the second displacement device can be transferred to the second guide element.

5. The displacement apparatus as claimed in claim 1, wherein the first displacement device includes a first carriage which can travel within or on the first guide element and the second displacement device includes a second carriage which can travel within or on the second guide element.

6. The displacement apparatus as claimed in claim 1, wherein the linking device is a parallel rocker, levers on the parallel rocker being connected to the first and second displacement device.

7. The displacement apparatus as claimed in claim 1, wherein the first guide element includes a first rail system and the second guide element includes a second rail system.

8. The displacement apparatus as claimed in claim 1, wherein the first displacement device is moveable approximately +/−200 mm around a central location.

9. The displacement apparatus as claimed in claim 1, wherein the first displacement device is moveable by a belt drive that is actively connected to the first displacement device.

10. The displacement apparatus as claimed in claim 1, wherein a portion of a leverage force acting on the first displacement device can be introduced to the second displacement device.

11. A C-arm system comprising:
   a C-arm having an x-ray emitter and x-ray detector; the C-arm having a displacement apparatus, the C-arm being arranged on the displacement apparatus in such a way that it can move in parallel with a patient support, wherein the displacement apparatus includes:
      a first guide element and a second guide element arranged in a single plane or in parallel to a single plane, the first and second guide elements being in vertical alignment with one another,
      a first displacement device arranged in a displaceable fashion along the first guide element,
      a second displacement device arranged in a displaceable fashion along the second guide element, and
      a linking device that connects the first and second displacement devices to one another in such a way that any movement in the first displacement device causes the second displacement device to move along the second guide element.

* * * * *